United States Patent [19]

Sprecker et al.

[11] 4,301,302
[45] * Nov. 17, 1981

[54] TETRAALKYL SUBSTITUTED TRICYCLIC KETONE

[75] Inventors: Mark A. Sprecker, Sea Bright; James M. Sanders, Eatontown; William L. Schreiber, Jackson; Hugh Watkins, Lincroft; Joaquin F. Vinals, Red Bank, all of N.J.; Edward J. Shuster, Brooklyn, N.Y.; Thomas J. O'Rourke, Red Bank, N.J.; Myrna L. Hagedorn, Highland Park, N.J.; Philip Klemarczyk, Old Bridge, N.J.

[73] Assignee: International Flavors & Fragrances Inc., New York, N.Y.

[*] Notice: The portion of the term of this patent subsequent to Feb. 10, 1998, has been disclaimed.

[21] Appl. No.: 206,617

[22] Filed: Nov. 13, 1980

Related U.S. Application Data

[63] Continuation-in-part of Ser. No. 95,149, Nov. 16, 1979, Pat. No. 4,250,338.

[51] Int. Cl.³ .................................................. C07C 49/453
[52] U.S. Cl. .................................. 568/373; 252/522 R; 568/665; 568/817; 424/69
[58] Field of Search ........................................ 568/373

[56] References Cited

U.S. PATENT DOCUMENTS 4,250,338  2/1981  Sprecker .............................. 568/343

Primary Examiner—G. T. Breitenstein
Assistant Examiner—Michael Shippin
Attorney, Agent, or Firm—Arthur L. Liberman

[57] ABSTRACT

Described is the compound having the structure:

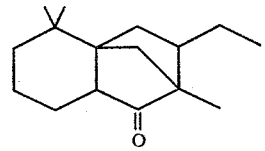

which is used as an intermediate in preparing compounds having organoleptic properties for augmenting or enhancing the aroma or taste of consumable materials, which compounds have the structures:

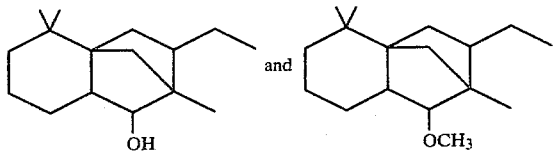

1 Claim, No Drawings

TETRAALKYL SUBSTITUTED TRICYCLIC KETONE

This application is a continuation in part of Application for U.S. Letters Patent Ser. No. 095,149 filed on Nov. 16, 1979 now U.S. Pat. No. 4,250,338 issued on Feb. 10, 1981.

BACKGROUND OF THE INVENTION

This invention relates to compounds having the generic structure:

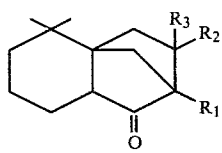

wherein $R_1$, $R_2$ and $R_3$ are the same or different and each represents hydrogen or C1–C3 lower alkyl, processes for preparing same and organoleptic uses thereof in perfumes, colognes, perfumed articles such as anionic, cationic and nonionic detergents and dryer-added fabric softeners and in smoking tobaccos and smoking tobacco articles which comprise a wrapper encasing a smoking tobacco body and impinging thereupon a smoking tobacco article filter.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Low-keyed, oily, woody amber, leathery, warm spice, earthy, camphoraceous, patchouli-like, balsamic, green, cardamom-like, vetiver-like, sweet woody, amber and minty aromas are desirable in several types of perfume compositions, perfumed articles such as anionic, cationic and non-ionic detergents, cosmetic powders and dryer-added fabric softener articles, and colognes.

Sweet, floral, woody, spicy, leathery and amber aromas prior to smoking and sweet, natural tobacco-like tastes and aromas are desirable in several types of smoking tobaccos, smoking tobacco articles and in smoking tobacco flavoring compositions.

British Pat. No. 896,039 entitled "Method of Producing Derivatives of the 1,1-Dimethyloctahydronaphthalene Series" discloses the generic process:

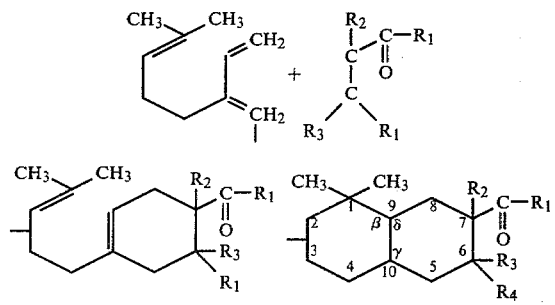

wherein $R_2$, $R_3$, and $R_4$ are disclosed to be same or different hydrogen atoms or alkyl and $R_1$ is disclosed to be hydroxy, alkyl or alkoxy. The British patent discloses this process to be useful for producing products "resembling the well known class of violet perfumes". Indeed, Example 5 of the British patent alleges that the compound 1,1,6,6-Tetramethyl-7-ketomethyl-Octalin produced by (1) reacting myrcene and mesityl oxide thermally followed by (2) subsequent cyclization, has a pleasant "woody ambergris smell". However, a repetition of the teachings of this British patent gives rise to the following results:

STRUCTURE OF COMPOUND

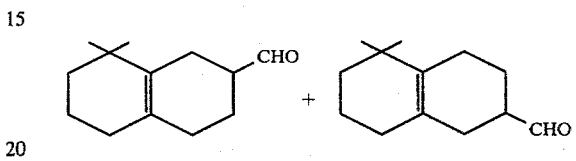

NAME:

1',2',3',4',5',6',7',8'-octahydro-8',8'(and 5',5')dimethyl-2'-naphthaldehyde

PERFUME PROPERTIES:

Green, fruity

STRUCTURE OF COMPOUND:

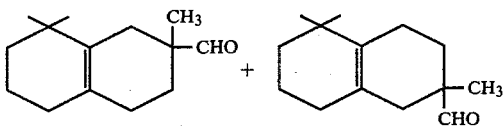

NAME:

1',2',3',4',5',6',7',8'-octahydro-2',8',8'(and 2',5',5')-trimethyl-2'-napthaldehyde

PERFUME PROPERTIES:

Green floral, fruity

STRUCTURE OF COMPOUND:

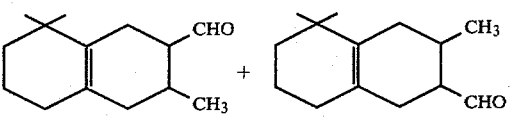

NAME:

1',2',3',4',5',6',7',8'-octahydro-3',8',8'(and 3',5',5')-trimethyl-2'-naphthaldehyde

PERFUME PROPERTIES:

Green, buttery, woody

U.S. Pat. No. 2,933,506, issued on Apr. 19, 1960, discloses the production of perfume compounds according to the reaction sequence:

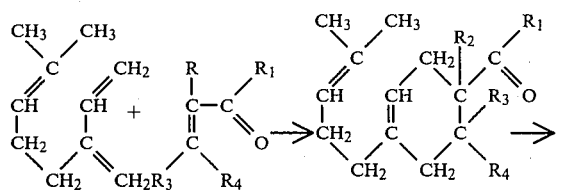

I  
myrcene

II  
dienophilic compound

III  
adduct

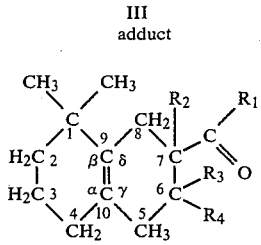

(a) β-isomer of 1,1-dimethyl octaline compound

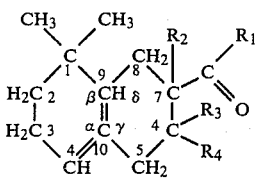

(b) α-isomer of 1,1-dimethyl octaline compound

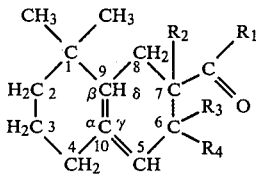

(c) γ-isomer of 1,1-dimethyl octaline compound

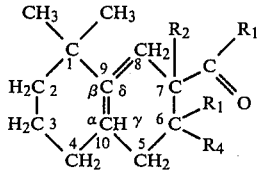

(d) δ-isomer of 1,1-dimethyl octaline compound

In said formula $R_1$, $R_2$, $R_3$, and $R_4$ represent hydrogen or alkyl, especially a lower alkyl radical, aryl, aralkyl, cycloalkyl, or heterocyclic residues. $R_1$ in said formula can also be the hydroxyl group or an ether group. The ether group may form an ester group or a lactone group with the —CO— group.

The new compounds are obtained by first subjecting myrcene of Formula I to the diene synthesis with a dienophilic compound of Formula II. The resulting adduct of Formula III is then subjected to ring closure reaction to form the corresponding 1,1-dimethyl octaline compounds of Formula IV.

Thus, for example, the 1,1-dimethyl-7-methylal octaline can be produced as follows:

576 g. (3 mols) of the aldehyde obtained from myrcene and acrolein, said aldehyde corresponding to Formula III wherein $R_1$, $R_2$, $R_3$, and $R_4$ are hydrogen, are dissolved in 600 cc. of ether. 279 g. (3 mols) of aniline dissolved in 500 cc. of ether are added to said solution portion by portion at room temperature in a separatory funnel while shaking the mixture repeatedly.

After allowing the mixture to stand at room temmperature for about 20 hours, the theoretical amount of water has split off. The resulting solution is separated from the water formed on reaction and is directly used for cyclization.

The ethereal solution of the Schiff's base is added drop by drop to 4 l. of 62% sulfuric acid at −15° C. within about 2 hours while stirring vigorously. Care must be taken that the termperature does not substantially exceed 0° C. After the solution has been added to the sulfuric acid, stirring of the reaction mixture is continued at −5° C. for about one hour. The reaction mixture is then treated with steam until all the solvent has been distilled off. The distillation requires about ½ hour. The reaction mixture has now separated into two layers. It is poured on ice and is exhaustively extracted with benzene. The benzene solution of the bicyclic aldehyde is washed with water until the wash water is substantially neutral. Thereafter, the solvent is distilled off under atmospheric pressure and the residue is subjected to fractional distillation in a vacuum.

In this manner 438 g. of 1,1-dimethyl-7-methylal octaline are obtained. The yield is about 76% of the theoretical yield. The reaction product consists to ⅔ of the β-compound with the double bond in 9,10-position and to ⅓ of a substantially uniform isomer, the double bond of which is either in α-, or in γ-, or in δ-position.

Characteristic properties of the mixture of isomers:
Boiling point: 85°–86° C./0.5 mm.;
Density $d_4^{20}$: 0.9877;
Index of refraction $n_D^{20}$: 1.5031;
Aldehyde content: 98–100%.

By fractional crystallization of the semicarbazones of the reaction mixture, the isomers can be separated from each other. For this purpose 70 g. of the bicyclic aldehyde mixture are mixed with a solution of 70 g. of semicarbazide hydrochloride and 70 g. of sodium acetate in 140 cc. of water. Methanol is added until complete solution is achieved. The reaction mixture is allowed to stand overnight at room temperature. 95.5 g. of an amorphous semicarbazone precipitates. It has an unsharp point of decomposition at 139°–141° C. On repeated recrystallization from 90% methanol, 53.5 g. of white crystals melting at 148° C. with decomposition are obtained.

In order to produce therefrom pure 1,1-dimethyl-7-methylal-$\Delta_{9,10}$-octaline, the semicarbazone was split up by heating with 50 g. of oxalic acid in 200 cc. of water. The aldehyde set free thereby is separated from the reaction solution by vacuum steam distillation. The steam distillate is subjected to fractional distillation in a vacuum. In this manner 30 g. of a very pure aldehyde are obtained. This aldehyde has a pleasant refreshing and sandalwood-like ionone odor.

Characteristic properties of 1,1-dimethyl-7-methylal-$\Delta_{9,10}$-octaline:
Boiling point: 85° C./0.5 mm.;
Density $d_4^{20}$: 0.9914;
Index of refraction $n_D^{20}$: 1.5054;
Aldehyde content: 100%.

After standing for several days at −25° C. there precipitates from the mother liquor of the semicarbazone reaction mixture a second compound which, on repeated recrystallization from methanol, has a melting point of 134° C. 14.5 g. of this semicarbazone are obtained. The aldehyde is set free therefrom by means of oxalic acid in the same manner as described hereinabove for the β-aldehyde.

The position of the double bond in said aldehyde could not yet be ascertained with certainty. The double bond is either in α-, γ-, or δ-position. The compound also has a refreshing ionone aroma, however, without any accompanying sandalwood-like nuance.

Characteristic properties of this isomeric aldehyde:
Boiling point: 85°–86° C./0.5 mm.,
Density $d_4^{20}$: 0.9890;
Index of refraction $n_D^{20}$: 1.5044;
Aldehyde content: 100%.

Another example indicating preparation of 1,1-dimethyl-7-methylal octaline in U.S. Pat. No. 2,933,506 is as follows:

1 mol. of the aldehyde in the form of its Schiff's base as prepared and used in Example 1 is dissolved in an equal amount of benzene. The benzene solution is added drop by drop to 700 cc. of 85% phosphoric acid at 0° C. while stirring vigorously. Thereafter, stirring of the reaction mixture is continued at 60° C. for 1 hour. Thereby not only cyclization is completed but the azomethine group is quantitatively split up. The resulting bicyclic aldehyde is then poured on ice, extracted by means of benzene, and the benzene layer is washed with water until neutral. After distilling off the solvent, 190 g. of residue of an aldehyde content of 82% are obtained. The crude bicyclic aldehyde is subjected to fractional distillation by means of a small fractionating column. In this manner 135 g. of 1,1-dimethyl-7-methylal octaline are obtained. The yield is about 70% of the theoretical yield. The aldehyde consists mainly of an isomer, the double bond of which is either in α-, or in γ-, or in δ-position.

Characteristic properties:
Boiling point: 96° C./0.7 mm.;
Density $d_4^{20}$: 0.9884;
Index of refraction $n_D^{20}$: 1.5042;
Aldehyde content: 98–100%.

Additional reaction of the resulting compounds with acid and heating gives rise to the compounds of our invention having the generic structure:

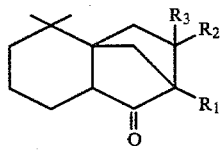

wherein $R_1$, $R_2$ and $R_3$ are the same or different and each represents hydrogen or C1–C3 lower alkyl.

However, there is no inference in any of the pertinent prior art that the tricyclic ketone compounds of our invention can be produced or ever have been produced.

THE INVENTION

It has now been discovered that novel smoking tobacco and smoking tobacco flavoring compositions having sweet, floral, woody, spicy, leathery and/or amber aroma and taste nuances prior to smoking and sweet natural tobacco tastes and aromas on smoking both in the main stream and the side stream, as well as novel perfume compositions, colognes and perfumed articles (e.g., solid or liquid anionic, cationic and non-ionic detergent compositions, as well as dryer-added fabric softener articles, as well as cosmetic powders) having intense and pleasant oily, woody amber, leathery, warm spice, earthy camphoraceous, patchouli-like, balsamic, green, cardamom-like, vetiver-like, sweet woody, amber and minty aromas may be provided by the utilization of one or more tricyclic ketone derivatives having the generic structure:

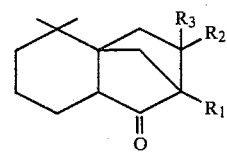

wherein each of $R_1$, $R_2$ and $R_3$ are the same or different and each represents hydrogen or C1–C3 lower alkyl, such as methyl, ethyl, n-propyl and i-propyl.

The novel tricyclic ketones of our invention useful as indicated supra, may be produced preferably by one of the following processes:

(1) First reacting myrcene having the structure:

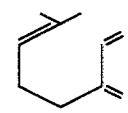

with an alpha, beta unsaturated aldehyde having the generic structure:

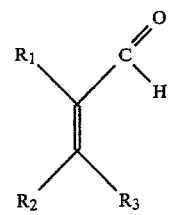

wherein $R_1$, $R_2$ and $R_3$ are the same or different hydrogen or lower alkyl in the presence of a Lewis acid catalyst such as aluminum trichloride, boron trifluoride, stannic fluoride, zinc fluoride zinc bromide, ethyl aluminum dichloride or diethyl aluminum monochloride or, in the absence of catalysts under conditions of higher temperatures, 50°–150° C., to produce an unsaturated aldehyde or a mixture of unsaturated aldehydes having the generic structure:

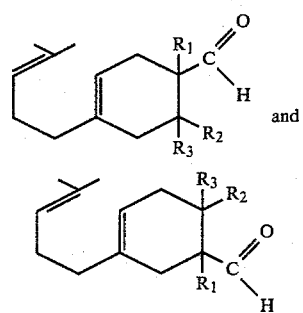

and

Depending upon the catalyst used, the proportion of one isomer to the other isomer of resulting aldehyde will vary.

The aldehydes having the generic structures:

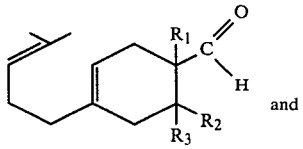 and

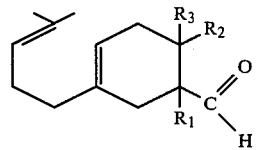

are either separated by standard means of physical separation, e.g., fractional distillation or industrial column chromatography, or they are permitted to remain as a mixture. These aldehydes are then reacted in the presence of acid, such as phosphoric acid or sulfuric acid, in order to produce cyclic aldehydes having the generic structure:

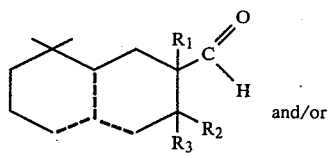 and/or

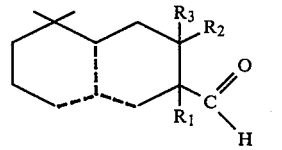

wherein one of the dashed lines represents a carbon-carbon double bond and each of the other dashed lines represents carbon-carbon single bonds, and wherein $R_1$, $R_2$ and $R_3$ are the same or different hydrogen or C1-C3 lower alkyl.

When the aldehyde having the structure:

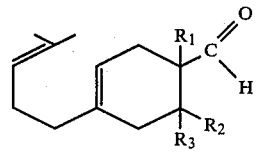

is reacted alone, the resulting aldehyde has the generic structure:

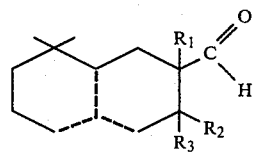

and is, of course, a mixture of aldehydes. Insofar as our invention is concerned, the only useful aldehyde to be reacted for producing compounds having the generic structure:

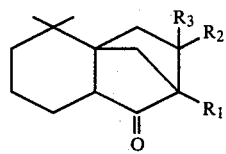

is the aldehyde having the structure:

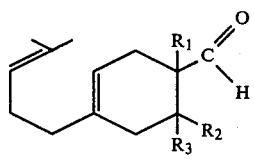

This aldehyde will form the mixture of aldehydes having the structure:

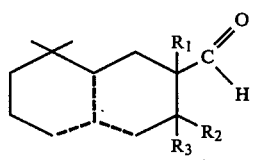

which in turn is reacted under acid conditions, (either Lewis acid or mineral acid) to form the tricyclic ketone having the structure:

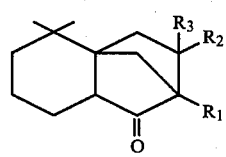

according to the mechanism:

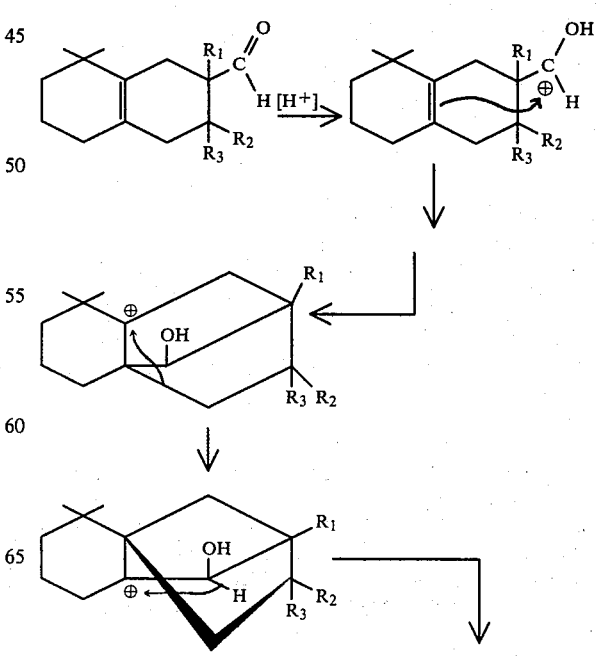

-continued

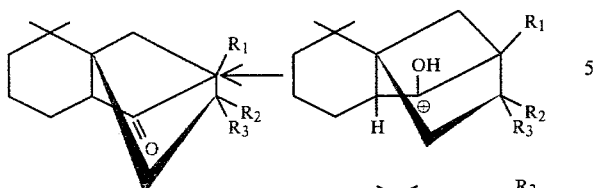

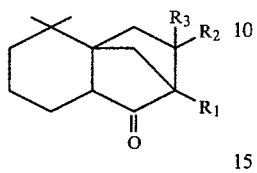

In the alternative, the aldehyde having the structure:

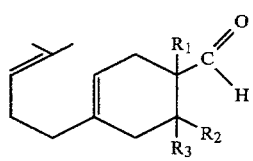

may first be reacted with an amine R'NH$_2$ to form an imine having the generic structure:

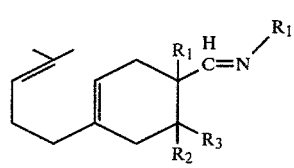

which in turn is cyclized in the presence of mineral acid or Lewis acid to form the mixtures of compounds having the structures:

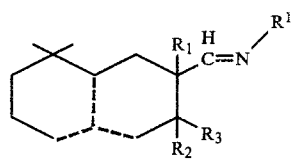

wherein R' is lower alkyl and $R_1$, $R_2$ and $R_3$ are the same or different hydrogen or lower alkyl and one of the dashed lines is a carbon-carbon double bond and each of the other dashed lines represents carbon-carbon single bonds.

The resulting mixture of aldehydes having the structure:

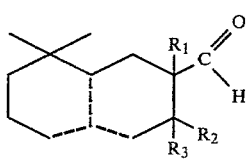

but not the mixture of aldehydes having the structure:

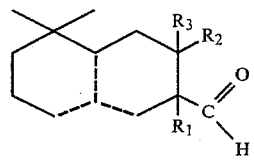

or the resulting imine having the structure:

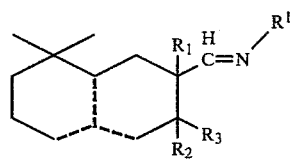

is thus reacted to form the novel compounds of our invention having the structure:

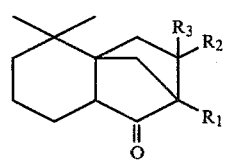

in the presence of acid.

The condition for the Diels-Alder reaction between myrcene, having the structure:

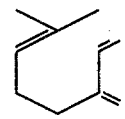

and the alpha, beta unsaturated aldehyde, having the structure:

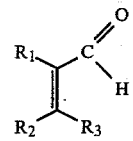

as well as the conditions for the reaction of the compounds having the structures:

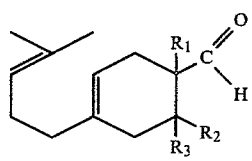

and

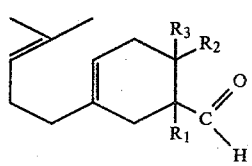

to form the cyclic compounds having the structures:

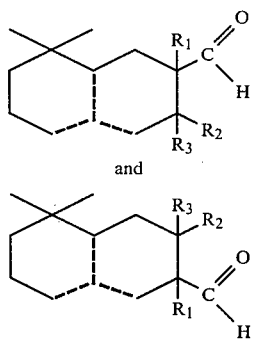

and are set forth in the literature as follows:
1. U.S. Pat. No. 3,911,018 issued on Oct. 7, 1975, at Columns 7, 8 and 9 thereof.
2. U.S. Pat. No. 2,933,506 issued on Apr. 19, 1960, at Examples 1, 2 and 3 at Columns 6, 7 and 8 thereof.

In the reaction to form the tricyclic ketone having the structure:

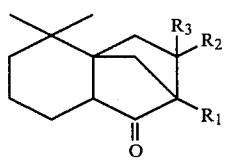

from the aldehyde having the structure:

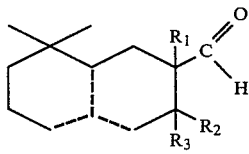

the mineral acids which can be used are hydrochloric acid, sulfuric acid, phosphoric acid, or paratoluene sulfonic acid. An inert solvent is used in this reaction, xylene, toluene, benzene or diethylbenzene, or a chlorocarbon such as chloroform (CHCl₃) or methylene chloride (CH₂Cl₂).

The mole ratio of aldehyde having the structure:

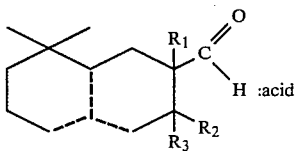

may vary from 1:10 up to 10:1 with a range of mole ratios of from about 1:2 up to about 1:0.5 being preferred.

The temperature of reaction may vary from 25° C. up to 100° C. with a temperature range from about 60° C. up to about 80° C. being preferred.

In place of the mineral acid being used, a Lewis acid may be used, such as aluminum chloride, stannic chloride, titanium tetrachloride, boron trifluoride, or boron trifluoride etherate, ethyl aluminum chloride, ethyl aluminum dichloride, zinc bromide or zinc chloride. The temperature of reaction may vary from 25° C. up to 100° C. with a temperature of from 25° C. to 45° C. being preferred. The mole ratio of aldehyde having the structure:

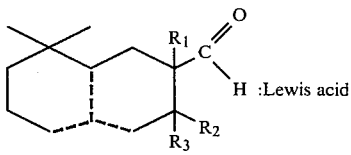

may vary from 1:1 up to 1:2 with an inert solvent being used which is either toluene, benzene, xylene, diethylbenzene, chloroform or methylene chloride.

The time of reaction for forming of the compounds represented by the generic structure:

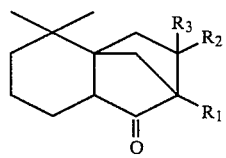

using the compounds represented by the generic structure:

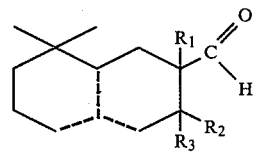

may vary from about 1 hour up to about 12 hours when operating at reflux temperatures, such as 110°–120° C., using a toluene solvent. Preferred is a reaction time of between 5 and 12 hours.

It is noteworthy that whereas the genus of compounds having the structure:

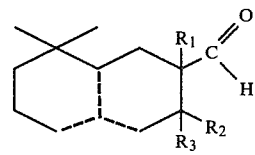

will react to form the genus of compounds having the structure:

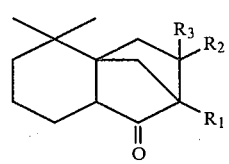

the genus of compounds having the structure:

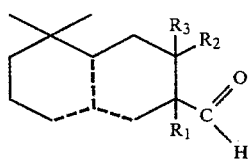

will not so react when treated with either Lewis acid or mineral acid under high temperature conditions. This gives rise to the advantage of separating out the isomeric components of compounds having the structures:

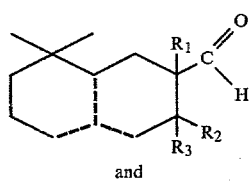

and

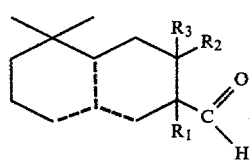

or compounds having the structures:

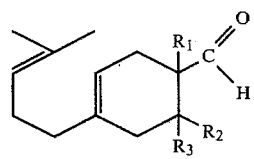

and

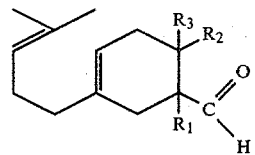

Examples of the tricyclic ketone compounds having the generic structure:

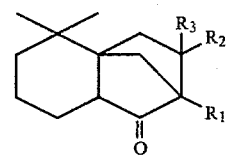

produced according to the processes of our invention and their organoleptic properties are set forth in the following table:

TABLE I

| STRUCTURE | NAME OF COMPOUND | PERFUMERY EVALUATION | SMOKING TOBACCO FLAVOR EVALUATION |
|---|---|---|---|
| 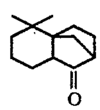 | hexahydro-5,5-dimethyl-2H-2,4-a-methanonaphthalene-1(5H)-one | A sweet, woody, camphoraceous aroma with minty and ambery nuances. |  |
| 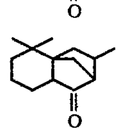 | hexahydro-2,5,5-trimethyl-2H-2,4-a-methanonaphthalene-1(5H)-one | A low-keyed, oily, woody, amber aroma with woody and slightly leathery undertones. On purification a deep woody, earthy camphoraceous, patchouli-like aroma with amber and leathery undertones. | Prior to smoking a sweet, floral, musty, woody, spicy and leathery and amber-like aroma and taste. On smoking, a sweet, floral, musty, woody, spicy, leathery, amber-like aroma with a slight cooling effect in both the main stream and the side stream. When added to a filter, a sweet aroma with enchanced tobacco taste and aroma of a very natural quality is obtained in the main stream and the side stream. |
| 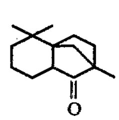 | hexahydro-1,5,5-trimethyl-2H-2,4-a-methanonaphthalene-1(5H)-one | A woody aroma with green, tart, cardamom-like undertones. |  |
| 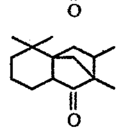 | hexahydro-1,2,5,5-tetramethyl-2H-2,4-a-methanonaphthalene-1(5H)-one | A sweet woody, camphoraceous, balsamic aroma with patchouli and deep woody undertones. | A floral ionone-like aroma with woody, balsamic nuances prior to and on smoking both in the main stream and the side stream. |

One or more of the tricyclic ketones of our invention and one or more auxiliary perfume ingredients including, e.g., alcohols, aldehydes, ketones other than the tricyclic ketones of our invention, terpenic hydrocarbons, nitriles, esters, lactones, natural essential oils and synthetic essential oils, may be admixed so that the combined odors of the individual components produce a pleasant and desired fragrance, particularly in the woody, ambery, leathery, patchouli-like and vetiver fragrances. Such perfume compositions usually contain (a) the main note or the "bouquet" or foundation stone of the composition; (b) modifiers which round off and accompany the main note; (c) fixatives which include odorous substances which lead a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more tricyclic ketone derivative(s) of our invention can be used to alter, modify or enhance the aroma characteristics of a perfume composition, for example, by utilizing or moderating the olfactory reaction contributed by another ingredient in the composition.

The amount of tricyclic ketone derivative(s) of our invention which will be effective in perfume compositions as well as in perfumed articles and colognes depends on many factors, including the other ingredients, their amounts and the effects which are desired. It has been found that perfume compositions containing as little as 0.01% of tricyclic ketone derivative(s) or even less (e.g., 0.005%) can be used to impart a vetiver aroma with sweet woody, citrusy, musky, woody/peppery, woody/leathery, hay and green nuances to soaps, cosmetics, detergents, powders and colognes. The amount employed can range up to 70% of the fragrance components and will depend on considerations of cost, nature of the end product, the effect desired on the finished product and the particular fragrance sought.

The tricyclic ketone derivative(s) of our invention are useful [taken along or together with other ingredients in perfume compositions] as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of tricyclic ketone derivative(s) will suffice to impart intense oily, woody amber, leathery, warm spice, earthy camphoraceous, patchouli-like, balsamic, green, cardamom-like, vetiver-like, sweet woody, ambery and minty aromas to various formulations such as vetiver formulations. Although, generally, no more than 60% of the tricyclic ketone derivative(s), based on the ultimate end product, is required in the perfume composition, amounts of tricyclic ketone derivative(s) of up to 95% may be used in such perfume composition.

When used in perfumed articles such as anionic, cationic and non-ionic detergents, or dryer-added fabric softener articles, cosmetic powders or deodorant compositions, from 0.1% up to 5.0% by weight of the tricyclic ketone based on the over-all perfumed article weight may be used in the perfumed articles to impart intense oily, woody amber, leathery, warm spice, earthy camphoraceous, patchouli-like, balsam-like, green, car- damom-like, vetiver-like, sweet woody, amber and minty aromas.

In addition, the perfume composition or fragrance composition of our invention can contain a vehicle, or carrier for the tricyclic ketone derivative(s). The vehicle can be a liquid such as a non-toxic alcohol, a non-toxic glycol, or the like. The carrier can also be an absorbent solid, such as a gum (e.g., gum arabic) or components for encapsulating the composition (such as gelatin).

An additional aspect of our invention provides an organoleptically improved smoking tobacco product and additives therefor, as well as methods of making the same which overcome problems heretofore encountered in which specific sweet, floral, woody, spicy, leathery and amber flavor characteristics of natural smoking tobacco (prior to and on smoking in both the mainstream and the sidestream) as well as cooling effects, are created, enhanced, modified or augmented and may be readily controlled and maintained at the desired uniform level regardless of variations in the tobacco components of the blend.

In carrying out this aspect of our invention, we add to smoking tobacco compositions or a suitable substitute therefor (e.g., dried lettuce leaves), or we add to the wrapper used in producing smoking tobacco articles which surround a cylindrical formed body of smoking tobacco, or we add to the filter which is in intimate contact with both the wrapper and the cylindrical shaped body of tobacco, an aroma and flavor additive containing as an active ingredient one or more of the tricyclic ketones of our invention.

In addition to the tricyclic ketone(s) of our invention other flavoring and aroma additives may be added to the smoking tobacco material or substitute therefor either separately or in mixture with the ketone(s) as follows:

I. Synthetic Materials

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho-(2,1-b)-furan
4-Hydroxyhexanoic acid, gamma lactone; and
Polyisoprenoid hydrocarbons defined in Example V of U.S. Pat. No. 3,589,372 issued on June 29, 1971.

II. Natural Oils

Celery seed oil;
Coffee extract;
Bergamot Oil;

Cocoa extract;
Nutmeg Oil; and
Origanum Oil.

An aroma and flavoring concentrate containing one or more tricyclic ketone derivative(s) of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes and/or cooling notes and/or floral, woody, spicy, leathery or amber notes, we have found that satisfactory results are obtained if the proportion by weight of the sum total of tricyclic ketone derivative(s) to smoking tobacco material is between 50 ppm and 1,500 ppm (0.015%–0.15%). We have further found that satisfactory results are obtained if the proportion by weight of the sum total of tricyclic ketone derivative(s) used to flavoring material is between 1,500 and 15,000 ppm (0.15%–1.5%).

Any convenient method for incorporating the tricyclic ketone derivative(s) into the tobacco product may be employed. Thus, the tricyclic ketone derivative(s) taken alone or along with other flavoring additives may be dissolved in a suitable solvent such as ethanol, diethyl ether and/or volative organic solvents and the resulting solution may either be spread on the cured, cased and blended tobacco material or the tobacco material may be dipped into such solution. Under certain circumstances, a solution of the tricyclic ketone derivative(s) taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the tricyclic ketone derivative(s) in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of hexahydro-2,5,5-trimethyl-2H-2,4-a-methanonaphthalene-1(5H)-one having the structure:

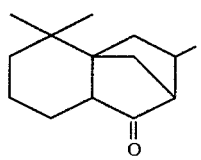

in an amount to provide a tobacco composition containing 800 ppm by weight of hexahydro-2,5,5-trimethyl-2H-2,4-a-methanonaphthalene-1(5H)-one on a dry basis. Thereafter, the alcohol is removed by evaporation and the tobacco is manufactured into cigarettes by the usual techniques. The cigarette when treated as indicated has a desired and pleasant aroma which is detectable in the main and sidestreams when the cigarette is smoked. The aroma is described as being sweeter, more aromatic, more tobacco-like and having sweet, woody, amber notes.

While our invention is particularly useful in the manufacture of smoking tobacco, such as cigarette tobacco, cigar tobacco and pipe tobacco, other tobacco products, formed from sheeted tobacco dust or fines may also be used. Likewise, the tricyclic ketone derivative(s) of our invention can be incorporated with materials such as filter tip materials (e.g., cellulose acetate filters wherein sweet, woody, piney and/or cooling effects are desired), seam paste, packaging materials and the like which are used along with tobacco to form a product adapted for smoking. Furthermore, the tricyclic ketone derivative(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

It will thus be apparent that the tricyclic ketone(s) of our invention can be utilized to alter, modify or enhance sensory properties, particularly organoleptic properties, such as flavor(s) and/or fragrance(s) of a wide variety of consumable materials, such as smoking tobacco, perfumed articles and perfumed compositions in colognes.

The following examples serve to illustrate processes for specifically producing the tricyclic ketone(s) of our invention and processes for utilizing said tricyclic ketone(s) for their organoleptic properties.

All parts and percentages given herein are by weight unless otherwise specified.

EXAMPLE I

Preparation of
Hexahydro-1,5,5-Trimethyl-2-Ethyl-2H-2,4-2-Methanonaphthalene-1(5H)-One

EXAMPLE I(A)

Reaction:

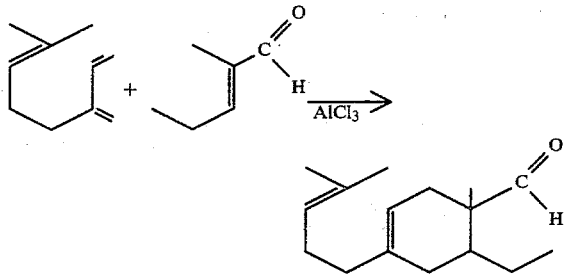

Into a 3 liter reaction flask equipped with stirrer, condenser, thermometer and dropping funnel is placed 500 cc of toluene and 294.0 grams (3.0 moles) of 2-methyl-2-pentenal. Slowly, 40.0 grams (0.3 moles) of aluminum chloride is added to the reaction mass. Dropwise over a period of 30 minutes while maintaining the reaction temperature at 20°–30° C. is added 3.0 moles (582.8 grams) of myrcene (70%). The reaction mass is stirred at 25°–30° C. for a period of 3.5 hours. At the end of the 3.5 hours, 500 cc of water is added to the reaction mass followed by 200 cc of 20% aqueous hydrochloric acid (purpose to break the emulsion). The resulting organic and inorganic layers are separated and the organic layer is stripped of solvent and distilled, yielding the following fractions (12 inch stone column):

| Fraction Number | Vapor Temp. °C. | Liquid Temp. °C. | Head Vac. mm. Hg | Weight of Fraction |
|---|---|---|---|---|
| 1 | 80/100 | 140/150 | 1.7/1.2 | 30.0 |
| 2 | 125 | 155 | 1.2 | 14.0 |
| 3 | 140 | 160 | 1.6 | 40.0 |
| 4 | 145 | 165 | 1.6 | 79.0 |
| 5 | 145 | 195 | 2.0 | 160.0 |
| 6 | 155 | 240 | 2.5 | 125.0 |

EXAMPLE I(B)

Reaction:

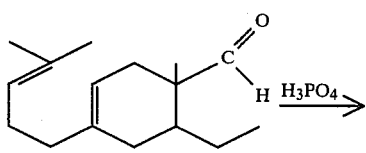 H₃PO₄ →

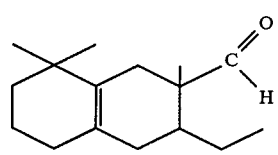

Into a 2 liter reaction vessel equipped with stirrer, condenser, thermometer and dropping funnel is placed 160.0 grams (1.74 moles) of toluene. The aldehyde produced in Example X(a) (400 grams/1.74 moles) is then added to the toluene. Dropwise over a period of 30 minutes 200 grams (1.74 moles) of phosphoric acid is added. The reaction mass is stirred for 8 hours. At the end of the 8 hour period 400 cc of water is added to the reaction mass and the organic and inorganic layers are separated. The organic layer is stripped of solvent and distilled on a 12 inch stone column yielding the following fractions:

| Fraction Number | Vapor Temp. °C. | Liquid Temp. °C. | Head Vac. mm. Hg | Weight of Fraction |
|---|---|---|---|---|
| 1 | 70/110 | 130/135 | 0.9/0.9 | 17.0 |
| 2 | 125 | 145 | 0.9 | 119.0 |
| 3 | 130 | 150 | 0.9 | 112.0 |
| 4 | 130 | 210 | 0.9 | 100.0 |

EXAMPLE I(C)

Reaction:

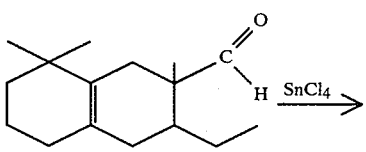 SnCl₄ →

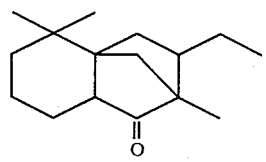

Into a 1000 cc reaction flask equipped with stirrer, condenser, thermometer and dropping funnel is placed 200 cc of toluene and 331.0 grams (1.396 moles) of the aldehyde prepared according to Example X(B). Dropwise over a period of 30 minutes, 36.29 grams (0.1396 moles) of concentrated stannic chloride solution is added while maintaining the reaction temperature at 30° C. The reaction mass is then heated for a period of 3 hours at 50° C. The reaction mass is then added to 250 cc of water and the resulting organic and inorganic layers are separated. The organic layer is washed with two 200 cc volumes of water and the organic organic layer is then stripped of solvent and distilled on a 12 inch stone column yielding the following fractions:

| Fraction Number | Vapor Temp. °C. | Liquid Temp. °C. | Head Vac. mm. Hg | Weight of Fraction |
|---|---|---|---|---|
| 1 | 120/125 | 140/155 | 1.0/1.0 | 41.0 |
| 2 | 135 | 160 | 1.0 | 110.0 |
| 3 | 155 | 220 | 1.0 | 85.0 |

EXAMPLE II

Preparation of 3-Ethyl-Octahydro-2,5,5-Trimethyl-2H-2,4A-Methanonaphthalene-1-ol

EXAMPLE II(A):

Reaction:

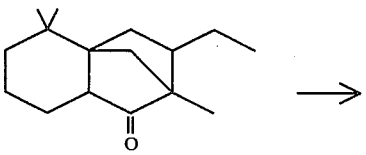 →

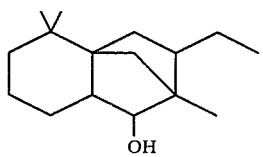

Into a 2000 cc reaction vessel fitted with stirrer, condenser, thermometer and dropping funnel is placed 200 cc of anhydrous tetrahydrofuran. 40 grams (1.0 moles) of 95% lithium aluminum anhydride is then added to the tetrahydrofuran. The resulting mixture is stirred and the tricyclic ketone produced according to Example I(C) is added dropwise over a period of 30 minutes while maintaining the reaction mass at 25°-30° C. The reaction mass is then stirred at room temperature for 2 hours. Infra-red analysis indicates that the reaction is complete and the organic layer is extracted, stripped of solvent and distilled yielding the following fractions:

| Fraction Number | Vapor Temp. °C. | Liquid Temp. °C. | Head Vac. mm. Hg | Weight of Fraction |
|---|---|---|---|---|
| 1 | 95/120 | 140/140 | 2.0/2.0 | 10.0 |
| 2 | 130 | 140 | 2.0 | 44.0 |
| 3 | 133 | 166 | 2.0 | 35.0 |
| 4 | 134 | 168 | 2.0 | 79.0 |
| 5 | 125 | 220 | 2.0 | 8.0 |

The distillation is carried out on a 12 inch stone packed column.

EXAMPLE II(B)

Reaction:

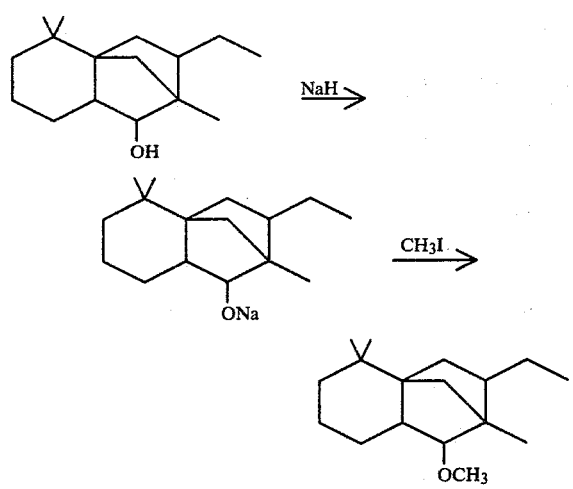

Into a 2000 cc reaction vessel equipped with stirrer, condenser, thermometer and dropping funnel is placed 200 cc of tetrahydrofuran and 36.0 grams (0.752 moles) of 50% sodium hydride. 176.0 grams (0.752 moles) of tricyclic alcohol prepared according to Example II(A) is dissolved in tetrahydrofuran and the resulting solution is added dropwise over a 20 minute period to the reaction mass with stirring. No exotherm occurs. The reaction mass is then refluxed and monitored using infra-red analysis to completion. The time of refluxing is 4 hours. The reaction mass at the end of the 4 hour period is then cooled to room temperature and over a period of 30 minutes 106.0 grams (0.752 moles) of methyl iodide is added dropwise. The reaction mass exotherms to 40° C. The reaction mass is then refluxed for a period of 8 hours whereupon infra-red analysis indicates that the reaction to form the ether is complete. The reaction mass is cooled and hydrolized with 200 cc of water and the organic phase is separated from the aqueous phase. The organic phase is washed with two 200 cc portions of water, dried, stripped of solvent and distilled on a 12 inch "Rushover" column yielding the following fractions:

| Fraction Number | Vapor Temp. °C. | Liquid Temp. °C. | Head Vac. mm. Hg | Weight of Fraction |
|---|---|---|---|---|
| 1 | 125/130 | 135/140 | 0.9/0.9 | 14.0 |
| 2 | 125 | 140 | 0.6 | 36.0 |
| 3 | 125 | 140 | 0.6 | 40.0 |
| 4 | 125 | 150 | 0.6 | 40.0 |
| 5 | 125 | 200 | 0.6 | 18.0 |
| 6 | 140 | 220 | 1.2 | 10.0 |

EXAMPLE III

Preparation of a Cosmetic Powder Preparation

A cosmetic powder is prepared by mixing in a ball mill, 100 grams of talcum powder with 0.25 grams of one of the substances set forth in Table I below. The resulting cosmetic powder has a pleasant aroma as set forth in Table I below.

TABLE I

| Structure of Reaction Product | Fragrance Properties |
|---|---|
| (structure with OH) Prepared according to Example II(A). | A woody, cedarwood-like and minty aroma profile. |
| (structure with OCH₃) Prepared according to Example II(B) | A woody, patchouli aroma profile. |

EXAMPLE IV

Perfumed Liquid Detergent

Concentrated liquid detergents (Lysine salt of n-dodecylbenzene sulfonic acid as more specifically described in U.S. Pat. No. 3,948,818, issued on Apr. 6, 1976) with fragrance profiles as defined in Table II below are prepared containing 0.10%, 0.15%, 0.20%, 0.25%, 0.30% and 0.35% of the substance as set forth in Table II below. They are prepared by adding and homogeneously mixing the appropriate quantity of substance as set forth in Table II below in the liquid detergent. The detergents all possess excellent intense aromas as defined according to the profiles of Table II below, the intensity increasing with greater concentrations of said substance as set forth below in Table II:

TABLE II

| Structure of Reaction Product | Fragrance Properties |
|---|---|
| (structure with OH) Prepared according to Example II(A). | A woody, cedarwood-like and minty aroma profile. |
| (structure with OCH₃) Prepared according to Example II(B) | A woody, patchouli aroma profile. |

EXAMPLE V

Preparation of a Cologne and Handkerchief Perfume

Substances set forth in Table III below are each individually incorporated into colognes at concentrations of 2.0%, 2.5%, 3.0%, 3.5%, 4.0%, 4.5% and 5.0% in (75%, 80%, 85% and 90% aqueous food grade ethanol); and into handkerchief perfumes at concentrations of 15%, 20%, 25% and 30% (in 95% aqueous food grade ethanol). Distinctive and definitive long-lasting warm aromas as defined according to Table III below are all imparted to the cologne and to the handkerchief perfumes at all levels as indicated above:

TABLE III

| Structure of Reaction Product | Fragrance Properties |
| --- | --- |
| [structure with OH] Prepared according to Example II(A). | A woody, cedarwood-like and minty aroma profile. |
| [structure with OCH₃] Prepared according to Example II(B) | A woody, patchouli aroma profile. |

EXAMPLE VI

Preparation of Soap Composition

One hundred grams of soap chips (IVORY®, produced by the Procter & Gamble Company, Cincinnati, Ohio) are admixed with one gram of the substance as set forth in Table IV below until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest excellent, long-lasting, warm aromas as set forth in the Table IV below:

TABLE IV

| Structure of Reaction Product | Fragrance Properties |
| --- | --- |
| [structure with OH] Prepared according to Example II(A). | A woody, cedarwood-like and minty aroma profile. |
| [structure with OCH₃] Prepared according to Example II(B) | A woody, patchouli aroma profile. |

EXAMPLE VII

Preparation of Solid Detergent Compositions

Detergents are prepared from the following ingredients according to Example I of Canadian Pat. No. 1,007,948:

| Ingredient | Percent by Weight |
| --- | --- |
| Neodol® 45-11 (a $C_{14}$–$C_{15}$ Alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of said detergent is admixed with 0.10, 0.15, 0.20 and 0.25 grams of the substance as set forth in Table V below. Each of the detergent samples have excellent, warm aromas as indicated in Table V below:

TABLE V

| Structure of Reaction Product | Fragrance Properties |
| --- | --- |
| [structure with OH] Prepared according to Example II(A). | A woody, cedarwood-like and minty aroma profile. |
| [structure with OCH₃] Prepared according to Example II(B) | A woody, patchouli aroma profile. |

EXAMPLE VIII

Utilizing the procedure of Example I of Column 15 of U.S. Pat. No. 3,632,396, a non-woven cloth substrate useful as a dryer-added fabric softening article of manufacture prepared wherein the substrate, the substrate coating and the outer coating and the perfuming material are as follows:

1. a water "dissolvable" paper ("Dissolvo Paper")
2. Adogen 448 (m.p. about 140° F.) as the substrate coating; and
3. an outer coating having the following formulation (m.p. about 150° F.):
   57% $C_{20-22}$ HAPS
   22% isopropyl alcohol
   20% antistatic agent
   1% of one of the substances as set forth in Table VI below Fabric softening compositions containing substances as set forth in Table VI below essentially consist of a substrate having a weight of about 3 grams per 100 square inches of substrate coating, of about 1.85 grams per 100 square inches of substrate, and an outer coating of about 1.4 grams per 100 square inches of substrate, thereby providing a total aromatized substrate and outer coating weight ration of about 1:1 by weight of the substrate. The aromas as set forth in Table VI below, are imparted in a pleasant manner, to the head space in the dryer on operation thereof, using the said dryer-added fabric softening non-woven fabric:

TABLE VI

| Structure of Reaction Product | Fragrance Properties |
|---|---|
| 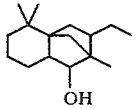<br>OH<br>Prepared according to Example II(A). | A woody, cedarwood-like and minty aroma profile. |
| 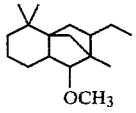<br>OCH₃<br>Prepared according to Example II(B) | A woody, patchouli aroma profile. |

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac division of AKZO of Chicago, Illinois.

EXAMPLE IX

Four drops of one of the substances set forth in Table VII below is added to two grams of Aromox ® DMC-W to produce a clear premix. The clear premix is added to 200 grams of CLOROX ® with stirring resulting in a clear stable, single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table VII below. Furthermore, no such characteristic "hypochlorite" aroma is retained on the hands of the individual handling such laundry in both the wet and the dry states:

TABLE VII

| Structure of Reaction Product | Fragrance Properties |
|---|---|
| 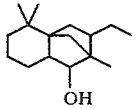<br>OH<br>Prepared according to Example II(A). | A woody, cedarwood-like and minty aroma profile. |
| 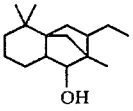<br>OCH₃<br>Prepared according to Example II(B) | A woody, patchouli aroma profile. |

EXAMPLE X

Aromox ® DMMC-W in various quantities is mixed with 0.1 grams of one of the substances set forth in Table VIII below. The resulting premixes are then added to 200 grams of an aqueous 5% sodium hypochlorite solution. Sufficient 12.5 M aqueous NaOH is added to bring the pH of the mixture up to 13. The following results are obtained:

| Percentage Aromox ® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table VIII below. Furthermore, no such characteristic "hypochlorite" aroma is retained on the hands of the individual handling such laundry in both the wet and the dry states:

TABLE VIII

| Structure of Reaction Product | Fragrance Properties |
|---|---|
| 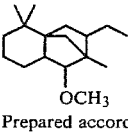<br>OH<br>Prepared according to Example II(A). | A woody, cedarwood-like and minty aroma profile. |
| 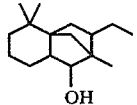<br>OCH₃<br>Prepared according to Example II(B) | A woody, patchouli aroma profile. |

EXAMPLE XI

Two grams of Aromox ® DMMC-W is admixed with eight drops of one of the substances set forth in Table IX below. The premix is then added with stirring to 200 grams of a 7% aqueous solution to lithium hypochlorite. Sufficient 3 M aqueous LiOH is added to bring the pH of the solution to 13.4. The mixture is then heated to 120° F. and maintained at that temperature with stirring for a period of 1 week. The resulting solution remains clear in a single phase. When used as a laundry bleach, the resulting bleached laundry, on dry-out in an atmosphere of 50% relative humidity retains a "clean" warm aroma as set forth in Table IX below; whereas without the use of the substance set forth in Table IX below, the bleached laundry has a faint characteristic disagreeable "hypochlorite" aroma.

TABLE IX

| Structure of Reaction Product | Fragrance Properties |
|---|---|
| 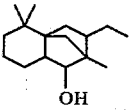<br>OH<br>Prepared according to Example II(A). | A woody, cedarwood-like and minty aroma profile. |

TABLE IX-continued

| Structure of Reaction Product | Fragrance Properties |
|---|---|
| [structure with OCH₃] Prepared according to Example II(B) | A woody, patchouli aroma profile. |

EXAMPLE XII

Two grams of Aromox® DMMC-W is admixed with eight drops of one of the substances of Table X below. This premix is then added, with stirring to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh" warm aroma as set forth in Table X below; whereas without the use of the substance set forth in Table X below, the bleached laundry has a faint characteristic disagreeable "hypochlorite" aroma:

TABLE X

| Structure of Reaction Product | Fragrance Properties |
|---|---|
| [structure with OH] Prepared according to Example II(A). | A woody, cedarwood-like and minty aroma profile. |
| [structure with OCH₃] Prepared according to Example II(B) | A woody, patchouli aroma profile. |

EXAMPLE XIII

Two grams of Aromox® DMMC-W is admixed with eight drops of one of the substances set forth in Table XI below. This premix is then added with stirring to 200 grams of a mixture containing 4.5% aqueous sodium hypochlorite and 4.5% aqueous lithium hypochlorite. Sufficient 2 M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting bleached laundry, on dry-out in an atmosphere of 50% relative humidity, retains an aroma as set forth in Table XI below. Whereas without the use of the substance set forth in Table XI below, the bleached laundry has a faint characteristic disagreeable "hypochlorite" aroma.

TABLE XI

| Structure of Reaction Product | Fragrance Properties |
|---|---|
| [structure with OH] Prepared according to Example II(A). | A woody, cedarwood-like and minty aroma profile. |
| [structure with OCH₃] Prepared according to Example II(B) | A woody, patchouli aroma profile. |

EXAMPLE XIX

Four drops of one of the substances set forth in Table XII below is added to 1.5 grams of Aromox® NCMDW to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm, long-lasting aroma as set forth in Table XII below. Furthermore, no such characteristic "hypochlorite" aroma is retained on the hands of the individual handling such laundry in both the wet and the dry states.

TABLE XII

| Structure of Reaction Product | Fragrance Properties |
|---|---|
| [structure with OH] Prepared according to Example II(A). | A woody, cedarwood-like and minty aroma profile. |
| [structure with OCH₃] Prepared according to Example II(B) | A woody, patchouli aroma profile. |

EXAMPLE XX

Four drops of one of the substances set forth in Table XIII below is added to 1 gram n-undecyl dimethyl amine oxide to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table XIII below. Furthermore, no such characteristic "hypochlorite" aroma is retained on the hands of the individual handling such laundry in both the wet and the dry states.

TABLE XIII

| Structure of Reaction Product | Fragrance Properties |
|---|---|
| 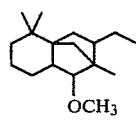<br>OH<br>Prepared according to Example II(A). | A woody, cedarwood-like and minty aroma profile. |
| <br>OCH₃<br>Prepared according to Example II(B) | A woody, patchouli aroma profile. |

EXAMPLE XXI

Four drops of one of the substances as set forth in Table XIV below are added to 1 gram of n-dodecyl dimethyl amine oxide to produce a clear premix. The clear premix is added to 200 grams of CLOROX® with stirring resulting in a clear, stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" aroma, but does have a warm, pleasant, long-lasting aroma as set forth in Table XIV below. Furthermore, no such characteristic "hypochlorite" aroma is retained on the hands of the individual handling such laundry in both the wet and the dry states.

TABLE XIV

| Structure of Reaction Product | Fragrance Properties |
|---|---|
| <br>OH<br>Prepared according to Example II(A). | A woody, cedarwood-like and minty aroma profile. |
| <br>OCH₃<br>Prepared according to Example II(B) | A woody, patchouli aroma profile. |

EXAMPLE XXII

One gram of n-tridecyl dimethyl amine oxide is admixed with eight drops of one of the substances as set forth in Table XV below. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a warm, fresh aroma described in Table XV below; whereas without the use of one of the substances of Table XV below, the bleached laundry has a faint characteristic disagreeable "hypochlorite" aroma.

TABLE XV

| Structure of Reaction Product | Fragrance Properties |
|---|---|
| 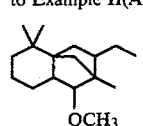<br>OH<br>Prepared according to Example II(A). | A woody, cedarwood-like and minty aroma profile. |
| <br>OCH₃<br>Prepared according to Example II(B) | A woody, patchouli aroma profile. |

EXAMPLE XXIII

A "soft-feel, good-hold" hair spray is produced containing the following ingredients:

| Ingredients | Parts by Weight |
|---|---|
| Polyvinylpyrrilidones/Vinyl acetate "E-735 Copolymer" manufactured by the GAF corporation of New York, N.Y. | 4.0 |
| Anhydrous Ethanol | 70.90 |
| Dioctyl Sebecate | 0.05 |
| Benzyl Alcohol | 0.05 |
| "Propellant A46" manufactured by the GAF corporation of New York, N.Y. | 24.95 |
| Fragrance ingredient as set forth in Table XVI below | 0.05 |

The PVP/VA copolymers are first dissolved in alcohol and all other ingredients are added until uniform. The propellant is then pressurized and used as an aerosol. The resulting hairspray has a pleasant aroma as set forth in Table XVI below:

TABLE XVI

| Structure of Reaction Product | Fragrance Properties |
|---|---|
| <br>OH<br>Prepared according to Example II(A). | A woody, cedarwood-like and minty aroma profile. |
| <br>OCH₃<br>Prepared according to Example II(B) | A woody, patchouli aroma profile. |

EXAMPLE XXIV

Scouring Cleanser Composition

A scouring cleanser composition is prepared in accordance with Example I, at columns 11 and 12 of U.S. Pat. No. 4,193,888, issued on Mar. 18, 1980. To this composition, a substance as set forth in Table XVII below is added at the level of 0.250% as set forth in the Table in said Example I of U.S. Pat. No. 4,193,888 yielding an aroma on using said cleanser in ordinary circumstances which is quite pleasant and described in said Table XVII as set forth below:

TABLE XVII

| Structure of Reaction Product | Fragrance Properties |
| --- | --- |
| 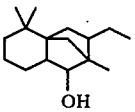<br>OH<br>Prepared according to Example II(A). | A woody, cedarwood-like and minty aroma profile. |
| 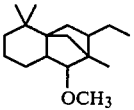<br>OCH₃<br>Prepared according to Example II(B) | A woody, patchouli aroma profile. |

EXAMPLE XXV

A fabric softening article prepared substantially as set forth in Examble VIII of Canadian Patent No. 1,069,260 is prepared, containing 0.21 percent by weight of a perfuming substance as set forth in Table XVIII below and yielding on use in a dryer, a faint aroma as set forth in Table XVIII below:

TABLE XVIII

| Structure of Reaction Product | Fragrance Properties |
| --- | --- |
| 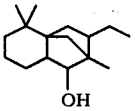<br>OH<br>Prepared according to Example II(A). | A woody, cedarwood-like and minty aroma profile. |
| 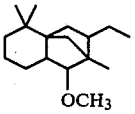<br>OCH₃<br>Prepared according to Example II(B) | A woody, patchouli aroma profile. |

What is claimed is:

1. The tricyclic ketone having the structure:

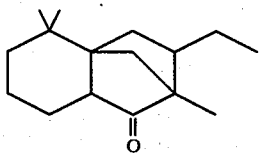

* * * * *

REEXAMINATION CERTIFICATE (495th)

United States Patent [19]

Sprecker et al.

[11] B1 4,301,302

[45] Certificate Issued * Apr. 29, 1986

[54] TETRAALKYL SUBSTITUTED TRICYCLIC KETONE

[75] Inventors: Mark A. Sprecker, Sea Bright; James M. Sanders, Eatontown; William L. Schreiber, Jackson; Hugh Watkins, Lincroft; Joaquin F. Vinals, Red Bank, all of N.J.; Edward J. Shuster, Brooklyn, N.Y.; Thomas J. O'Rourke, Red Bank, N.J.; Myrna L. Hagedorn, Highland Park, N.J.; Philip Klemarczyk, Old Bridge, N.J.

[73] Assignee: International Flavors & Fragrances Inc., New York, N.Y.

Reexamination Request:
No. 90/000,742, Mar. 15, 1985

Reexamination Certificate for:
Patent No.: 4,301,302
Issued: Nov. 17, 1981
Appl. No.: 206,617
Filed: Nov. 13, 1980

[*] Notice: The portion of the term of this patent subsequent to Feb. 10, 1998 has been disclaimed.

Related U.S. Application Data

[63] Continuation-in-part of Ser. No. 95,149, Nov. 16, 1979, Pat. No. 4,250,338.

[51] Int. Cl.⁴ .......................................... C07C 49/453
[52] U.S. Cl. ............................. 568/373; 252/522 R; 568/665; 568/817; 424/69
[58] Field of Search ......................................... 568/373

[56] References Cited

U.S. PATENT DOCUMENTS 2,933,506  4/1960  Ohloff ............................ 260/343.2

OTHER PUBLICATIONS

Baldwin et al., "Rearrangements in Lewis Acid Catalyzed Diels-Alder Reactions" *J. Org. Chem.*, vol. 44, No. 12, 1979, pp. 1923–1927.

*Primary Examiner*—Michael L. Shippen

[57] ABSTRACT

Described is the compound having the structure:

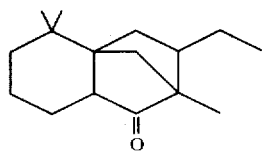

which is used as an intermediate in preparing compounds having organoleptic properties for augmenting or enhancing the aroma or taste of consumable materials, which compounds have the structures:

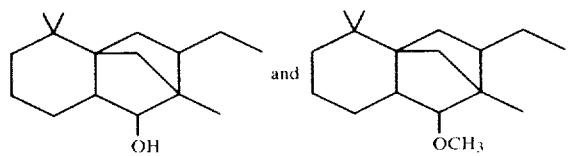

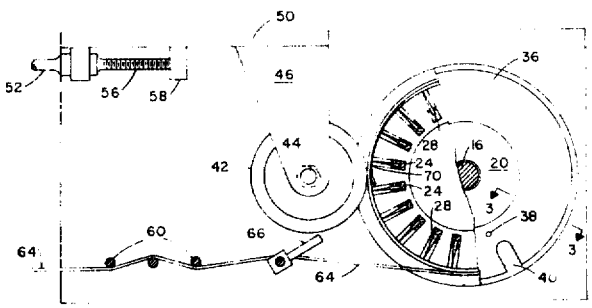

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

New claims 2-4 are added and determined to be patentable.

1. The tricyclic ketone having the structure:

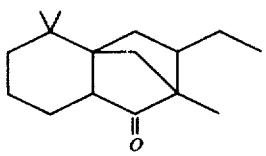

*in recovered form.*
*2. A product containing a substantial amount of the compound having the structure:*

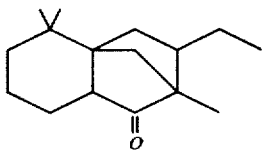

*prepared according to the process of treating the compound having the structure:*

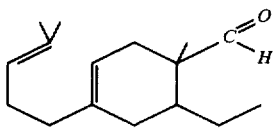

*with acid at elevated temperatures for a period of time such that a substantial quantity of the compound having the structure:*

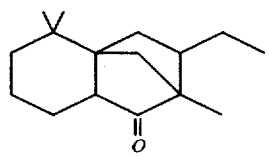

*is formed and then fractionally distilling the resulting reaction product whereby a composition of matter containing a substantial amount of compound having the structure:*

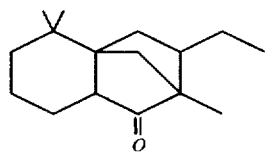

*is formed.*
*3. The product of claim 2 wherein in the process for preparing said product the temperature of reaction varies from 25° C. up to 100° C.*
*4. The product of claim 2 wherein the acid in the process for preparing the product is a Lewis acid and the Lewis acid is stannic chloride.*

* * * * *